United States Patent
Iijima et al.

(10) Patent No.: US 6,924,399 B2
(45) Date of Patent: Aug. 2, 2005

(54) METHOD OF MANUFACTURING DIMETHYL ETHER

(75) Inventors: Masaki Iijima, Tokyo (JP); Kazuto Kobayashi, Hiroshima (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 10/316,086

(22) Filed: Dec. 11, 2002

(65) Prior Publication Data

US 2003/0121200 A1 Jul. 3, 2003

(30) Foreign Application Priority Data

Dec. 28, 2001 (JP) ........................................ 2001-401509
Jan. 31, 2002 (JP) ........................................ 2002-024527

(51) Int. Cl.⁷ ............................................. C07C 41/09
(52) U.S. Cl. ...................................... 568/698; 568/699
(58) Field of Search ............................... 568/698, 699; 518/702, 704; 422/187, 235

(56) References Cited

U.S. PATENT DOCUMENTS

| | | | |
|---|---|---|---|
| 4,341,069 A | * 7/1982 | Bell et al. ...................... | 60/781 |
| 4,560,807 A | 12/1985 | Murai et al. .................. | 568/698 |
| 4,743,576 A | * 5/1988 | Schneider et al. ........... | 502/242 |
| 4,885,405 A | 12/1989 | Dornhagen et al. .......... | 568/698 |
| 4,913,842 A | * 4/1990 | Yoneoka et al. .............. | 252/373 |
| 5,297,620 A | * 3/1994 | Yabe et al. .............. | 165/104.12 |
| 5,316,627 A | 5/1994 | Hammer ....................... | 203/34 |
| 5,498,370 A | * 3/1996 | Bhattacharyya et al. .... | 252/373 |
| 5,750,799 A | 5/1998 | Van Dijk ..................... | 568/698 |

FOREIGN PATENT DOCUMENTS

| DE | 199 43 219 | 3/2001 |
|---|---|---|
| EP | 0 270 852 | 6/1988 |
| EP | 0 285 004 | 10/1988 |

OTHER PUBLICATIONS

Kikkawa et a., Dimethyl ether fuel proposed as an alternative to LNG, Oil & Gas Journal, Apr. 1998, vol. 96, ISS. 14, pp. 1–8 as supplied from Proquest.*

* cited by examiner

Primary Examiner—Rosalynd Keys
(74) Attorney, Agent, or Firm—Oblon, Spivak, McClelland, Maier & Neustadt, P.C.

(57) ABSTRACT

Dimethyl ether is obtained with at low cost by transporting methanol under room temperature and atmospheric pressure from the methanol producing district to the dimethyl ether consuming district or its neighboring district by converting the raw material containing the transported methanol into dimethyl ether in the consuming district or its neighboring district.

9 Claims, 3 Drawing Sheets

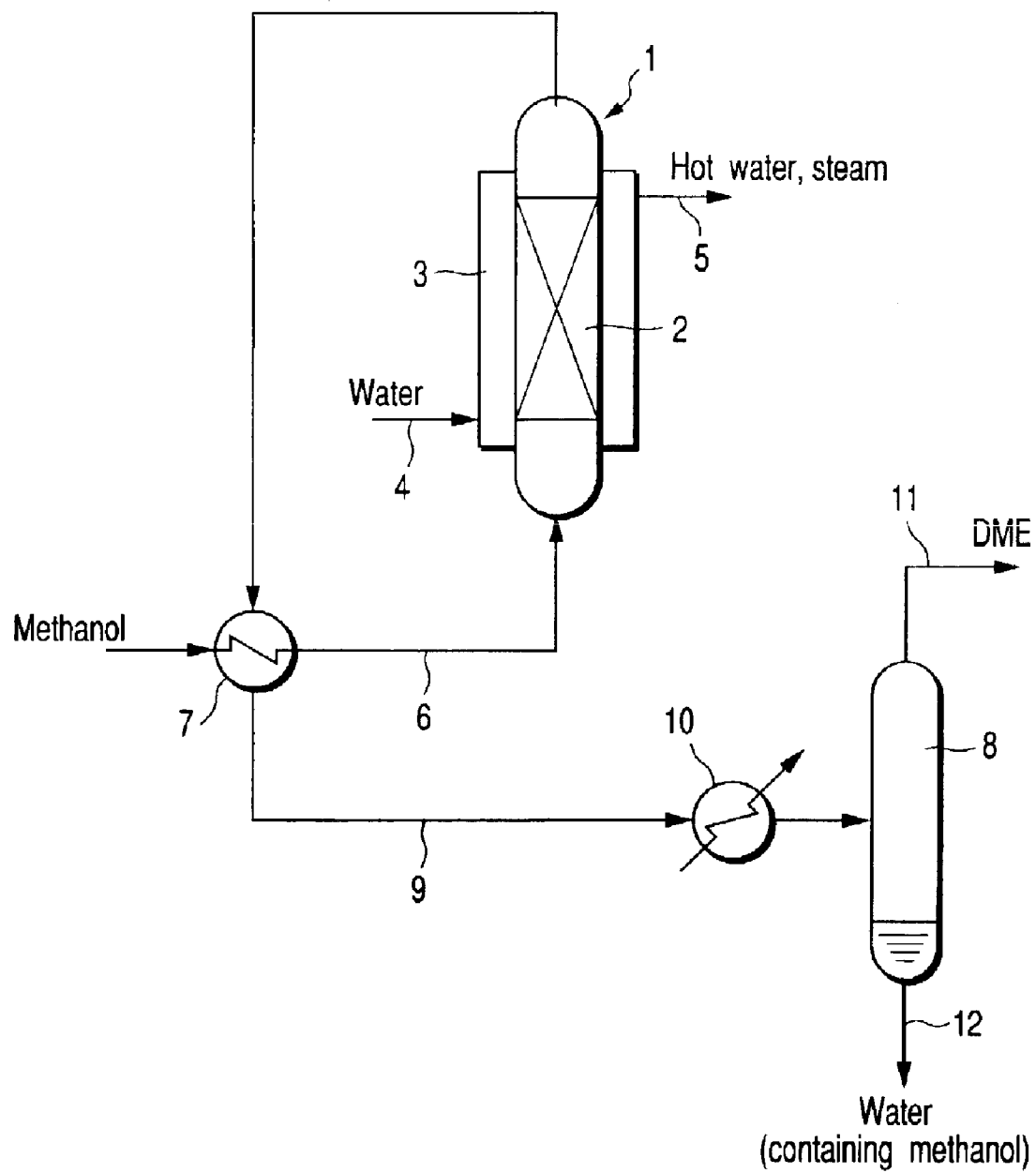
F I G. 1

METHOD OF MANUFACTURING DIMETHYL ETHER

CROSS-REFERENCE TO RELATED APPLICATIONS

This application is based upon and claims the benefit of priority from the prior Japanese Patent Applications No. 2001-401509, filed Dec. 28, 2001; and No. 2002-024527, filed Jan. 31, 2002, the entire contents of both of which are incorporated herein by reference.

BACKGROUND OF THE INVENTION

1. Field of the Invention

The present invention relates to a method of manufacturing dimethyl ether (DME).

2. Description of the Related Art

Liquefied petroleum gas (LPG), which is used as, for example, a fuel, is very costly. Specifically, the price of LPG, if delivered to the consuming district, e.g., household, is more than 10 times as high as the import price. Therefore, dimethyl ether attracts attention as a substitute for LPG in recent years, thus utilization studies are now being carried out.

It is customary to manufacture dimethyl ether in the producing district of a natural gas by using as the raw material a natural gas or methanol synthesized from the natural gas. The manufactured dimethyl ether is liquefied under a high pressure and the liquefied dimethyl ether is loaded in a high pressure tank or cylinder for transport to the consuming district. Alternatively, the manufactured dimethyl ether is cooled to temperatures lower than −25° C. and packed in a freezing tank under atmospheric pressure for transport to the consuming district.

However, dimethyl ether gives rise to the problems transportation and storage costs. Also, where dimethyl ether is stored in a high pressure tank, it is necessary to supervise the safety of the high pressure gas in the dimethyl ether producing district.

BRIEF SUMMARY OF THE INVENTION

The present invention is intended to provide a method of manufacturing dimethyl ether and supplying it to the consuming district at a low total cost. In the method of the present invention, a liquid methanol that can be handled easily is transported under room temperature and atmospheric pressure from the methanol producing district to the dimethyl ether consuming district, and dimethyl ether is manufactured in the district where it is consumed, which markedly lowers the transport and storage costs, thereby lowering the total cost.

The present invention is also intended to provide a method of manufacturing dimethyl ether, which permits converting the raw material containing methanol into dimethyl ether and also permits converting methanol contained in water separated and discharged from a distillation column into hydrogen and carbon dioxide by utilizing the heat generated in converting the methanol-containing raw material into dimethyl ether so as to effectively utilize the methanol.

According to a first aspect of the present invention, there is provided a method of manufacturing dimethyl ether, comprising transporting a raw material containing methanol under room temperature and under atmospheric pressure to the dimethyl ether consuming district or its neighboring district, and converting the methanol into dimethyl ether.

Further, according to a second aspect of the present invention, there is provided a method of manufacturing dimethyl ether comprising:

providing a manufacturing apparatus of dimethyl ether including an internal reactor loaded with a catalyst for synthesizing dimethyl ether, an external reactor arranged outside the internal reactor and loaded with a catalyst for decomposing methanol, and a distillation column connected to the internal reactor and the external reactor;

supplying a heated raw material containing methanol into the internal reactor for forming a reaction mixture;

supplying the reaction mixture into the distillation column so as to separate the reaction mixture into dimethyl ether and water containing methanol; and supplying the water containing methanol into the external reactor so as to decompose methanol into hydrogen and carbon dioxide.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the present invention, and together with the general description given above and the detailed description of the preferred embodiments given below, serve to explain the principles of the present invention.

FIG. 1 schematically shows the construction of a dimethyl ether manufacturing plant used in a first embodiment of the present invention;

DETAILED DESCRIPTION OF THE INVENTION

The method of the present invention for manufacturing dimethyl ether will now be described in detail.

(First Embodiment)

In the first step, methanol is produced in the producing district of a natural gas, such as the Middle or Near East, and transported to the dimethyl ether (DME) consuming district or neighboring district, under room temperature and atmospheric pressure. The transported methanol is converted into DME in the consuming district of DME.

The consuming district of DME or its neighboring district includes, for example, 1) the district in which is erected a city gas manufacturing plant utilizing DME as a substitute for an LPG for the heat control of the city gas, 2) the site in which is operated a taxi service utilizing DME in place of an LPG as a fuel of a diesel engine vehicle, 3) the site in which is sold DME housed in cylinders as a substitute for LPG, and 4) a household in which DME is utilized as a fuel.

For converting methanol into DME, methanol having a purity of, for example, 100% is used as a raw material, and the reaction is carried out in the presence of a catalyst for synthesizing DME, such as an alumina series catalyst, under temperatures of 240° C. to 320° C. and under an atmospheric pressure.

Figure 2:
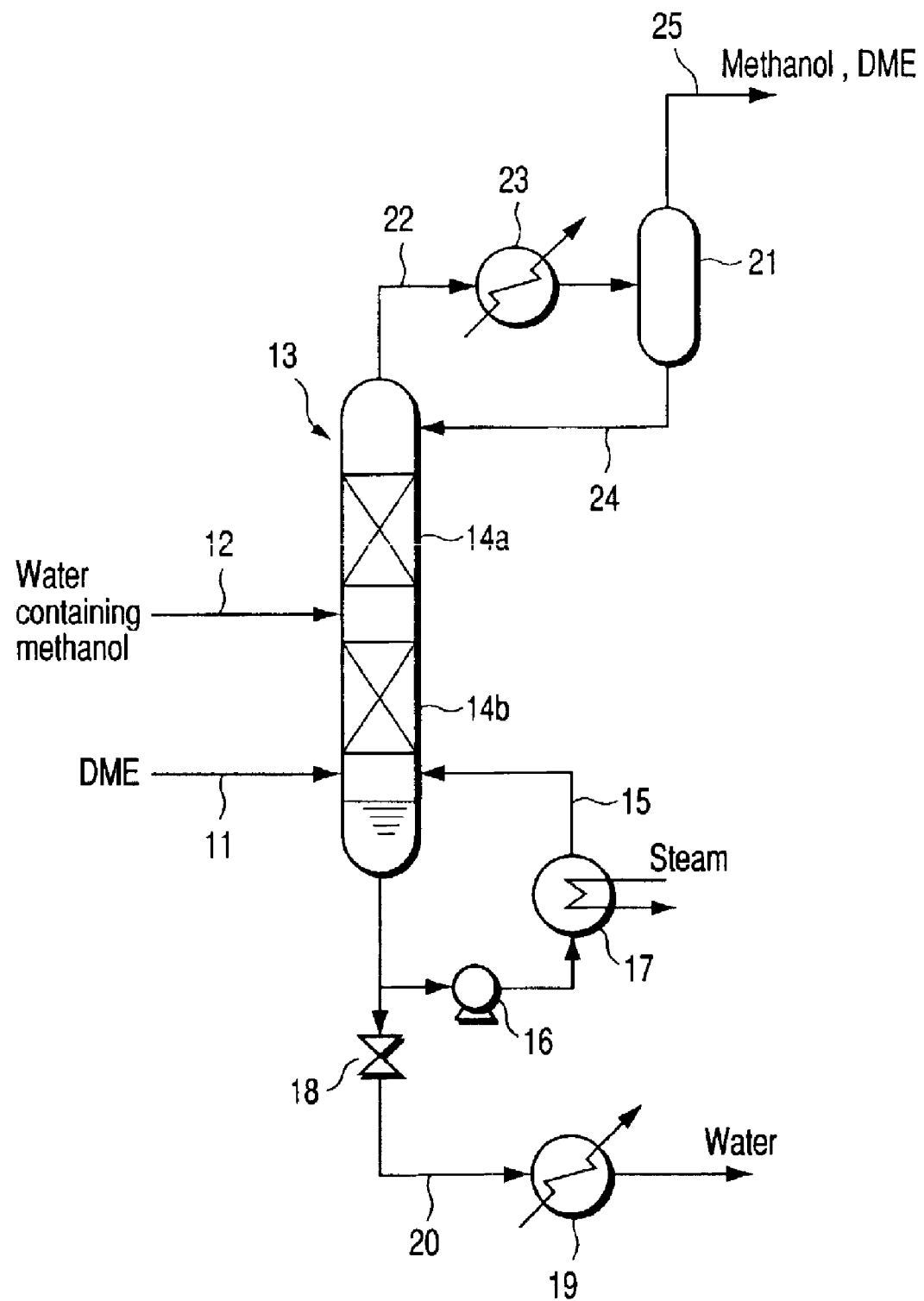
FIG. 2 schematically shows the construction of a methanol distillation column incorporated in the manufacturing plant shown in FIG. 1.

DME can be manufactured in a manufacturing plant, as shown in FIGS. 1 and 2.

The manufacturing plant shown in FIG. 1 comprises a reaction tower 1. A catalyst loading section 2 is arranged within the reaction tower 1, and a cooling chamber 3 in which is circulated a cooling fluid, e.g., water, is arranged to surround the outer surface of the reaction tower 1. A water supply passageway 4 is connected to a region in the vicinity of the bottom portion of the cooling chamber 3. On the other hand, a steam discharge passageway 5 is connected to an upper portion of the cooling chamber 3.

A raw material supply passageway 6 is connected to the bottom portion of the reaction tower 1. Also, a heat exchanger 7 is mounted to the raw material supply passageway 6.

A DME distillation column 8 is connected to the reaction tower 1 via a fluid passageway 9 connected to the upper portion of the reaction tower 1. The fluid passageway 9 extends to cross the heat exchanger 7. Further, a cooling device 10 is mounted to the fluid passageway 9.

The method of manufacturing DME will now be described with reference to the manufacturing plant shown in FIG. 1.

In the first step, methanol having a purity of, for example, 100%, which is heated to 240 to 320° C., is supplied into the reaction tower 1 through the raw material supply passageway 6, and DME is synthesized in the presence of a catalyst for synthesizing DME loaded in the loading section 2. The synthesizing reaction of DME is an exothermic reaction and, thus, it is possible to obtain a hot water or steam from the steam discharge passageway 5 by supplying water into the cooling chamber 3 through the water supply passageway 4.

The reaction mixture containing DME is supplied into the DME distillation column 8 through the fluid passageway 9. When the reaction mixture is circulated through the fluid passageway 9, a heat exchange is performed in the heat exchanger 7 between the reaction mixture and the raw material circulated through the raw material supply passageway 6, with the result that the reaction mixture is cooled and the raw material is heated. Further, the reaction mixture is cooled in the cooling device 10 and, then, supplied into the DME distillation column 8. The reaction mixture supplied into the DME distillation column 8 is separated into DME and water containing methanol. The separated DME is discharged from the top of the distillation column 8 through a fluid passageway 11. On the other hand, the separated water containing methanol is discharged from the bottom portion of the distillation column 8 through a fluid passageway 12.

Incidentally, it is possible to add a methanol distillation column 13 shown in FIG. 2 to the manufacturing plant shown in FIG. 1.

To be more specific, two loading members (or trays) 14a and 14b are arranged separately from each other in the vertical direction inside the methanol distillation column 13. A circulation passageway 15 is connected at one end to the bottom portion of the methanol distillation column 13 and at the other end to that portion of the methanol distillation column 13 which is positioned below the lower loading member 14b. A pump 16 and a heat exchanger 17 are mounted to the circulation passageway 15 in the order mentioned as viewed from the side of the bottom portion of the methanol distillation column 13. Also, a branched passageway 20 is branched from the circulation passageway 15, and a valve 18 and a cooling device 19 are mounted to the branched passageway 20.

The top portion of the methanol distillation column 13 is joined to a gas-liquid separator 21 via a fluid passageway 22, and a cooling device 23 is mounted to the fluid passageway 22. The gas-liquid separator 21 is joined to the upper side wall of the methanol distillation column 13 via a returning fluid passageway 24. Further, a fluid passageway 25 for discharging methanol and DME is connected to the gas-liquid separator 21.

The fluid passageway 11 for discharging DME, which is shown in FIG. 1, is connected to that portion of the methanol distillation column 13 which is positioned below the lower loading member 14b. Also, the fluid passageway 12 for discharging water containing methanol, which is shown in FIG. 1, is connected to that portion of the methanol distillation column 13 which is positioned between the upper and lower loading members 14a and 14b.

In the system shown in FIG. 2, DME and water containing methanol are supplied through the fluid passageways 11 and 12, respectively, into the methanol distillation column 13, with the valve 18 that is mounted to the branched passageway 20 closed. At the same time, the pump 18 is driven and, for example, steam is supplied into the heat exchanger 17 so as to heat the bottom portion of the distillation column 13. In this case, the DME supplied through the fluid passageway 11 is heated in the bottom portion of the methanol distillation column 13 so as to be moved upward within the distillation column 13. On the other hand, the methanol containing water, which is supplied through the fluid passageway 12, is stripped in the lower loading member 14b and the upper loading member 14a. By this stripping, methanol is distilled and, at the same time, the water containing undistilled methanol is stored in the bottom portion of the distillation column 13. The water containing the undistilled methanol, which is stored in the bottom portion of the distillation column 13, is circulated through the circulation passageway 15 by the driving of the pump 16. During the circulation, the water containing the undistilled methanol is heated in the heat exchanger 17 so as to distill methanol in the bottom portion of the distillation column 13.

Methanol containing steam and DME are circulated through the fluid passageway 22 connected to the top portion of the distillation column 13. During the circulation, methanol containing steam and DME are cooled by the cooling device 23 and, then, supplied into the gas-liquid separator 21. In the gas-liquid separator 21, methanol containing steam and DME are separated into methanol, DME and water. The separated methanol and DME are discharged and recovered through the fluid passageway 25, and the separated water is returned to the distillation column 13 through the returning fluid passageway 24.

In the distilling operation described above, the heated water stored in the bottom portion of the distillation column 13, the methanol content of said heated water being substantially zero, is discharged to the outside through the branched passageway 20 by opening the valve 18 and, then, cooled in the cooling device 19 mounted to the branched passageway 20.

Incidentally, when methanol transported in the first embodiment described above is converted into DME in the consuming district of DME, the conversion can be performed by the method according to second embodiment of the present invention described herein later.

According to the first embodiment of the present invention described above, methanol is transported under room temperature and atmospheric pressure from the dimethyl ether producing district to the consuming district, or its neighboring district, and the transported methanol is converted into DME in the consuming district. The particular method of the present invention is markedly advantageous in terms of transportation cost, over the conventional method in which DME is manufactured in the methanol producing district, then the manufactured DME is liquefied under a high pressure and the liquefied DME is housed in a high pressure tank or cylinder for transportation to the DME consuming district, or the manufactured DME is cooled to temperatures not higher than −25° C. and housed in a refrigeration tank under atmospheric pressure for transportation to the consuming district. As a result, the present invention produces prominent effects as summarized below:

1) It is possible for the owner of a city gas manufacturing plant using DME as a substitute for an LPG for the heat control of a city gas to manufacture a city gas at a low cost.

2) In the taxi service operation using DME in place of an LPG as a fuel for a diesel engine vehicle, it is possible to provide a fuel for the diesel engine vehicle at a low cost.

3) In the selling business of a fuel, in which DME is housed in a gas cylinder as a substitute for LPG, it is possible to sell the DME at a low cost.

4) In households that use DME, it can be used as a low cost fuel.

By using the manufacturing plant shown in FIG. 1 for the operation to convert the raw material containing methanol into DME, this can be done in the reaction tower 1. At the same time, it is possible to obtain a hot water and steam by supplying water into the cooling chamber 3 arranged to surround the reaction tower 1 so heat it is heated by the exothermic reaction carried out within the reaction tower 1.

Further, it is possible to recover methanol and to discharge water whose methanol content is substantially zero by adding the methanol distillation column 13 shown in FIG. 2 to the manufacturing plant shown in FIG. 1. Specifically, DME separated in the DME distillation column 8 is supplied into the middle portion of the methanol distillation column 13 through the fluid passageway 11, and the water containing methanol is supplied to the lower portion of the methanol distillation column 13 through the fluid passageway 12. At the same time, the lower portion of the distillation column 13 is heated so as to strip the water containing methanol so as to recover methanol and discharge the water whose methanol content is substantially zero.

(Second Embodiment)

Figure 3:
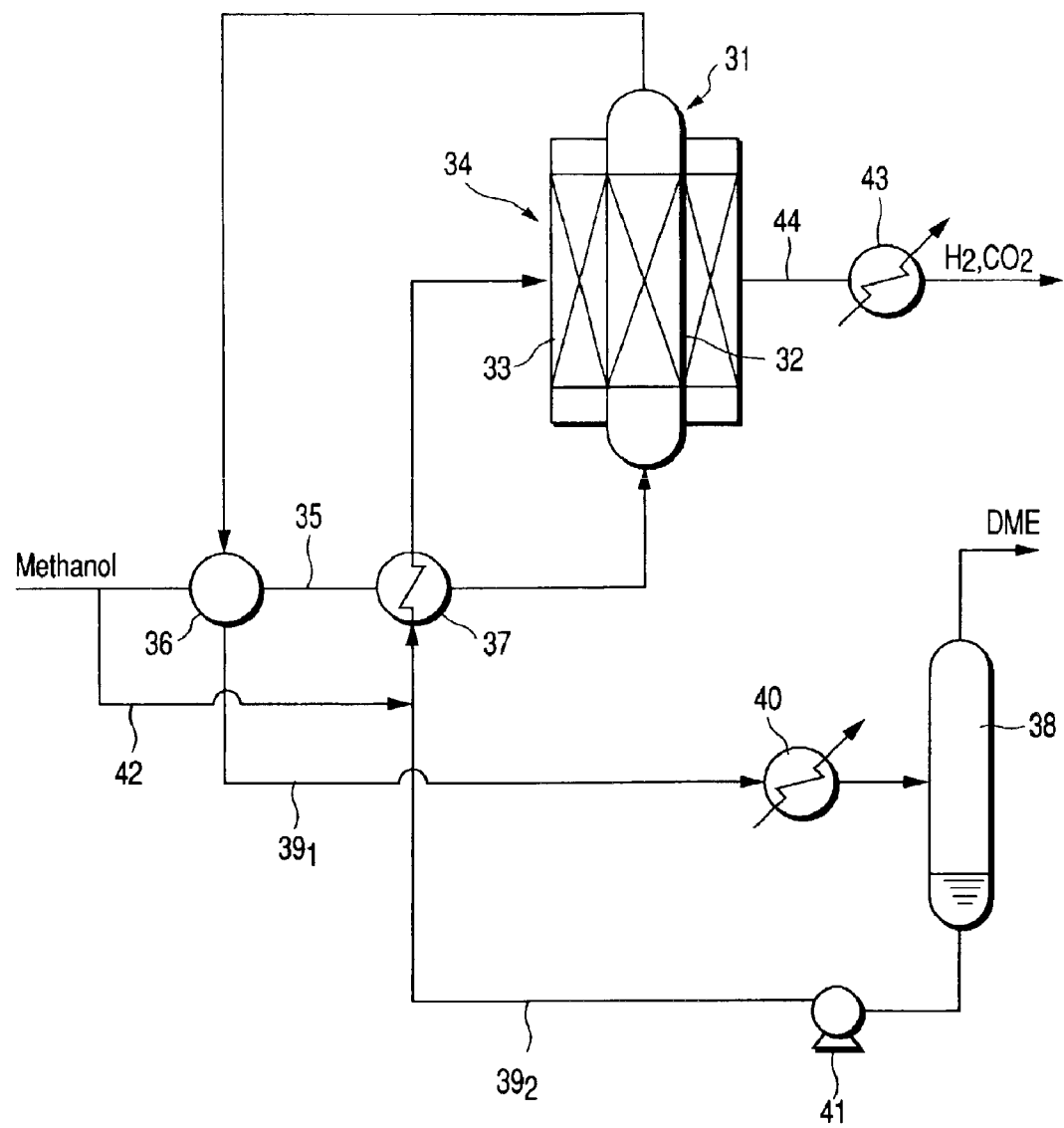
FIG. 3 schematically shows the construction of a dimethyl ether manufacturing plant used in a second embodiment of the present invention.

FIG. 3 schematically shows the construction of a dimethyl ether manufacturing plant used in the second embodiment of the present invention.

As shown in the drawing, the dimethyl ether manufacturing plant includes a cylindrical internal reactor 31. A loading section 32 of a DME synthesizing catalyst, such as an alumina series catalyst, is arranged within the internal reactor 31, and an annular external reactor 34 including a loading section 33 of a methanol reforming catalyst, such as a copper-based catalyst, is arranged to surround the outer surface of the internal reactor 31.

A raw material supply passageway 35 is connected to the bottom portion of the internal reactor 31. First and second heat exchangers 36, 37 are mounted to the raw material supply passageway 35.

A DME distillation column 38 is connected to the internal reactor 31 through a fluid passageway $39_1$ connected to the upper portion of the internal reactor 31. The fluid passageway $39_1$ extends to cross the first heat exchanger 36. A cooling device 40 is mounted to the fluid passageway $39_1$. The bottom portion of the distillation column 38 is connected to the external reactor 34 through a fluid passageway $39_2$. A pump 41 is mounted to the fluid passageway $39_2$ in the vicinity of the distillation column 38. Also, the fluid passageway $39_2$ extends to cross the second heat exchanger 37.

A branched raw material supply passageway 42 is branched from the raw material supply passageway 35 so as to be connected to the fluid passageway $39_2$. Further, a discharge passageway 44 having a cooling device 43 mounted thereto is connected to the external reactor 34.

The method of manufacturing DME by using the manufacturing plant shown in FIG. 3 will now be described.

In the first step, the raw material heated to 240 to 320° C., e.g., methanol having a purity of 100%, is supplied into the internal reactor 31 through the raw material supply passageway 35. As a result, DME is synthesized in the presence of a DME synthesizing catalyst such as an alumina-based catalyst in the loading section 32. The reaction to synthesize DME is an exothermic reaction.

The reaction mixture containing DME is supplied into the DME distillation column 38 through the fluid passageway $39_1$. While passing through the fluid passageway $39_1$, the reaction mixture exchanges heat within the first heat exchanger 36 with the raw material passing through the raw material supply passageway 35, with the result that the reaction mixture is cooled, and the raw material is heated. The reaction mixture is further cooled in the cooling device 40 and, then, supplied into the distillation column 38. The reaction mixture supplied into the distillation column 38 is separated into DME and water containing methanol. The separated DME is discharged from the top portion of the distillation column 38 so as to be recovered.

On the other hand, the water containing methanol is supplied by the driving of the pump 41 from the bottom portion of the distillation column 38 into the annular external reactor 34 through the fluid passageway $39_2$. While passing through the fluid passageway $39_2$, the water containing methanol exchanges heat within the second heat exchanger 37 with the raw material passing through the raw material supply passageway 35, with the result that the water is heated and the raw material is cooled. The methanol contained in the water supplied into the external reactor 34 is reformed in the presence of the methanol reforming catalyst in the loading section 33 so as to generate hydrogen and carbon dioxide. It should be noted that the methanol reforming reaction is an endothermic reaction, and the DME synthesizing reaction is an exothermic reaction. It follows that it is possible to maintain a good heat balance during the reactions so as to effectively utilize the heat.

Where the amount of methanol in the bottom portion of the distillation column 38 is small in the methanol reforming reaction described above, the raw material methanol is introduced from the raw material supply passageway 35 into the fluid passageway $39_2$, through which flows water containing methanol, via the branched raw material supply passageway 42.

The hydrogen and carbon dioxide formed in the external reactor 34 are discharged and recovered through the discharge passageway 44 having the cooling device mounted thereto.

As described above, according to the second embodiment of the present invention, the raw material containing methanol can be converted into DME, and the methanol contained in the water separated in and discharged from the distillation column can be effectively utilized.

To be more specific, in the general manufacturing process of dimethyl ether, methanol heated to 240° C. to 320° C. is supplied into a reaction tower, and DME is synthesized in the presence of a DME synthesizing catalyst such as an alumina-based catalyst in the loading section. As described previously, the reaction to synthesize DME is an exothermic reaction. The reaction mixture containing DME is cooled and, then, supplied into the DME distillation column so as to be separated into DME and water containing methanol. The separated DME is discharged from the top portion of the distillation column so as to be recovered, and the water containing methanol is discharged from the bottom portion of the distillation column.

When it comes to the conventional manufacturing process of dimethyl ether, the water discharged from the bottom portion of the DME distillation column certainly contains methanol. However, methanol contained in the discharged water is not effectively utilized but is discarded.

Under the circumstances, in the second embodiment of the present invention, the raw material containing methanol can be converted into DME within the internal reactor 31. At the same time, the methanol-containing water separated from the DME distillation column 38 is supplied into the annular external reactor 34 surrounding the internal reactor 31 so as to decompose methanol by utilizing the heat generated within the internal reactor 31 (exothermic reaction) and the methanol decomposing catalyst loaded in the external reactor 34, thereby obtaining mainly hydrogen. It follows that the raw material containing methanol can be converted into DME, and the methanol contained in the water separated in and discharged from the distillation column 38 can be effectively utilized.

It should also be noted that the raw material methanol used in the methanol decomposing reaction can be introduced from the raw material supply passageway 35 into the fluid passageway $39_2$, through which flows the methanol-containing water, via the branched raw material supply passageway 42. It follows that, even where the amount of methanol in the bottom portion of the distillation column 38 is small, it is possible to decompose methanol effectively so as to obtain hydrogen with a high stability.

Incidentally, in the second embodiment described above, the reactor loaded with a DME synthesizing catalyst is arranged inside, and the reactor loaded with a methanol decomposing catalyst is arranged outside. However, it is possible to reverse the positional relationship between these two reactors.

As described above in detail, the method of the present invention for manufacturing dimethyl ether makes it possible to transport methanol, which is liquid under room temperature and atmospheric pressure and, thus, can be handled easily, from the methanol producing district to the consuming district of dimethyl ether for manufacturing dimethyl ether in the consuming district. It follows that the transporting cost and the storing cost can be markedly lowered so as to make it possible to supply dimethyl ether of a low cost to, for example, the owner of a city gas manufacturing plant, the taxi service operator, the seller of dimethyl ether as a substitute for an LPG, and the household.

The present invention also provides a method of manufacturing dimethyl ether, which makes it possible to convert the raw material containing methanol into dimethyl ether and to convert the methanol contained in the water separated in and discharged from the distillation column into hydrogen by utilizing the heat generated from the reaction to synthesize dimethyl ether.

Additional advantages and modifications will readily occur to those skilled in the art. Therefore, the present invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing dimethyl ether comprising:
providing a manufacturing apparatus of dimethyl ether including an internal reactor loaded with a catalyst for synthesizing dimethyl ether, an external reactor arranged outside the internal reactor and loaded with a catalyst for decomposing methanol, and a distillation column connected to the internal reactor and the external reactor;
supplying a heated raw material containing methanol into said internal reactor for forming a reaction mixture;
supplying said reaction mixture into said distillation column so as to separate the reaction mixture into dimethyl ether and water containing methanol; and
supplying said water containing methanol into said external reactor so as to decompose methanol into hydrogen and carbon dioxide.

2. The method of manufacturing dimethyl ether according to claim 1, wherein methanol is added to said water containing methanol.

3. A method of manufacturing dimethyl ether, comprising transporting a raw material containing methanol under room temperature and under atmospheric pressure to the dimethyl ether consuming district or its neighboring district, and converting the methanol into dimethyl ether,
wherein the process of converting methanol into dimethyl ether in said dimethyl ether consuming district or its neighboring district is carried out by using a plant comprising an internal reactor loaded with a dimethyl ether synthesizing catalyst, an external reactor arranged to surround the outer surface of said internal reactor and loaded with a methanol decomposing catalyst, and a distillation column connected to said internal reactor and said external reactor such that a heated raw material containing methanol is supplied into said internal reactor so as to form a reaction mixture, the reaction mixture thus formed is supplied into said distillation column so as to be separated into dimethyl ether and water containing methanol, and said water containing methanol is supplied into said external reactor so as to be decomposed into hydrogen and carbon dioxide.

4. The method of manufacturing dimethyl ether according to claim 3, wherein said dimethyl ether consuming district or its neighboring district is the district in which is erected a city gas manufacturing plant using dimethyl ether as a substitute for an LPG for the heat control of the city gas.

5. The method of manufacturing dimethyl ether according to claim 3, wherein said dimethyl ether consuming district or its neighboring district is the district in which is operated a taxi service utilizing dimethyl ether in place of an LPG as a fuel for a diesel engine vehicle.

6. The method of manufacturing dimethyl ether according to claim 3, wherein said dimethyl ether consuming district or its neighboring district is the district in which is sold dimethyl ether, which is housed in a gas cylinder, as a substitute for an LPG.

7. The method of manufacturing dimethyl ether according to claim 3, wherein said dimethyl ether consuming district or its neighboring district is the household utilizing dimethyl ether as a fuel.

8. The method of manufacturing dimethyl ether according to any one of claims 3 to 7, wherein the process of converting methanol into dimethyl ether in said dimethyl ether consuming district or its neighboring district is carried out by using a plant comprising a reaction tower having a dimethyl ether synthesizing catalyst loaded therein and having a cooling fluid brought into contact with the outer surface thereof, a heated raw material containing methanol being supplied into said reaction tower, and said cooling fluid being brought into contact with said reaction tower so as to recover and utilize said cooling fluid as hot water or steam.

9. The method of manufacturing dimethyl ether according to claim 8, wherein the process of converting methanol into dimethyl ether in said dimethyl ether consuming district or its neighboring district is carried out by using a plant comprising a dimethyl ether distillation column into which the reaction mixture formed in said reaction tower is introduced and a methanol distillation column into which dimethyl ether and water containing methanol, which are separated in said dimethyl ether distillation column, are introduced such that the reaction mixture formed in said reaction tower is supplied into said dimethyl ether distillation column so as to be separated into dimethyl ether and water containing methanol, the separated dimethyl ether is supplied into the lower portion of said methanol distillation column, said water containing methanol is supplied into the middle portion of said methanol distillation column, and the lower portion of said methanol distillation column is heated so as to strip methanol contained in said water and, thus, to recover methanol and water separately.

* * * * *